United States Patent
Wuollett et al.

(10) Patent No.: US 9,408,913 B2
(45) Date of Patent: Aug. 9, 2016

(54) COMPOSITION AND DRESSING FOR WOUND TREATMENT

(75) Inventors: Michael Wuollett, Chanhassen, MN (US); Susan Wuollett, Chanhassen, MN (US)

(73) Assignee: Protege Biomedical, LLC, Chanhassen, MN (US)

( * ) Notice: Subject to any disclaimer, the term of this patent is extended or adjusted under 35 U.S.C. 154(b) by 14 days.

(21) Appl. No.: 14/344,403

(22) PCT Filed: Sep. 12, 2012

(86) PCT No.: PCT/US2012/054928
§ 371 (c)(1),
(2), (4) Date: Nov. 19, 2014

(87) PCT Pub. No.: WO2013/040080
PCT Pub. Date: Mar. 21, 2013

(65) Prior Publication Data
US 2015/0079152 A1 Mar. 19, 2015

Related U.S. Application Data

(60) Provisional application No. 61/533,484, filed on Sep. 12, 2011, provisional application No. 61/670,251, filed on Jul. 11, 2012.

(51) Int. Cl.
| | |
|---|---|
| A61K 47/02 | (2006.01) |
| A61L 15/44 | (2006.01) |
| C04B 35/185 | (2006.01) |
| A61L 15/18 | (2006.01) |
| A61L 15/20 | (2006.01) |
| A61K 38/36 | (2006.01) |
| A61K 33/06 | (2006.01) |
| A61L 15/14 | (2006.01) |
| A61L 26/00 | (2006.01) |
| C07K 14/745 | (2006.01) |

(52) U.S. Cl.
CPC ............ *A61K 47/02* (2013.01); *A61K 33/06* (2013.01); *A61K 38/36* (2013.01); *A61K 38/363* (2013.01); *A61L 15/14* (2013.01); *A61L 15/18* (2013.01); *A61L 15/20* (2013.01); *A61L 26/0004* (2013.01); *A61L 26/0066* (2013.01); *C04B 35/185* (2013.01); *A61L 2300/102* (2013.01); *A61L 2300/252* (2013.01); *A61L 2300/418* (2013.01); *A61L 2400/04* (2013.01); *C07K 14/745* (2013.01)

(58) Field of Classification Search
CPC ....... A61K 47/02; A61K 38/36; A61K 33/06; A61L 15/44; A61L 15/18; A61L 15/20; C04B 35/185
USPC ............... 424/445, 682; 423/327.2; 514/13.6
See application file for complete search history.

(56) References Cited

U.S. PATENT DOCUMENTS

| | | |
|---|---|---|
| 3,113,568 A | 12/1963 | Robins |
| 4,822,349 A | 4/1989 | Hursey et al. |
| 5,955,112 A | 9/1999 | Kaplan |
| 6,162,241 A * | 12/2000 | Coury et al. ............... 606/214 |
| 6,890,436 B2 | 5/2005 | Komatsu et al. |
| 7,595,429 B2 | 9/2009 | Hursey |
| 7,604,819 B2 | 10/2009 | Huey et al. |
| 7,858,123 B2 | 12/2010 | Stucky et al. |
| 7,968,114 B2 | 6/2011 | Huey et al. |
| 2002/0169476 A1 | 11/2002 | Cohen |
| 2003/0165560 A1 | 9/2003 | Otsuka et al. |
| 2006/0035087 A1 | 2/2006 | Yadav et al. |
| 2007/0154510 A1 | 7/2007 | Wilcher et al. |
| 2007/0264315 A1 | 11/2007 | Fournie et al. |
| 2007/0269499 A1 | 11/2007 | Hen et al. |
| 2008/0085300 A1 | 4/2008 | Huey et al. |
| 2008/0199539 A1 | 8/2008 | Baker et al. |
| 2008/0220050 A1* | 9/2008 | Chen et al. ............... 424/434 |
| 2009/0041859 A1 | 2/2009 | Mizutani et al. |
| 2009/0047329 A1 | 2/2009 | Stucky et al. |
| 2009/0123509 A1 | 5/2009 | Berkland et al. |
| 2009/0123525 A1 | 5/2009 | Bedard |
| 2009/0148502 A1 | 6/2009 | Pronovost |
| 2009/0186013 A1 | 7/2009 | Stucky et al. |
| 2009/0232902 A1 | 9/2009 | Liu et al. |
| 2009/0291124 A1 | 11/2009 | Bedard |
| 2009/0299253 A1 | 12/2009 | Hursey |
| 2010/0069813 A1 | 3/2010 | Crisp |
| 2010/0143421 A1 | 6/2010 | Van Reeth et al. |
| 2010/0221312 A1 | 9/2010 | Cohen et al. |

(Continued)

FOREIGN PATENT DOCUMENTS

| | | |
|---|---|---|
| WO | 2005007095 | 1/2005 |
| WO | 2007056671 | 5/2007 |

OTHER PUBLICATIONS

Mullite density: retrieved from internet: http://www.mindat.org/min-2806.html. Retrieved on Aug. 10, 2015.*

(Continued)

*Primary Examiner* — Ernst V Arnold
*Assistant Examiner* — Hong Yu
(74) *Attorney, Agent, or Firm* — Audrey J. Babcock; Briggs and Morgan, P.A.

(57) ABSTRACT

The invention provides methods and compositions for wound treatment and/or blood clot formation, e.g., arresting the flow of blood from an open wound. The methods and compositions provide for promoting and accelerating wound healing and optionally provide for inhibition of microbial infection and/or a local analgesic effect.

15 Claims, No Drawings

(56) References Cited

U.S. PATENT DOCUMENTS

| | | | |
|---|---|---|---|
| 2010/0292624 | A1 | 11/2010 | Diegelmann et al. |
| 2011/0002971 | A1 | 1/2011 | Hassler et al. |
| 2011/0046262 | A1 | 2/2011 | Bublewitz et al. |
| 2011/0064785 | A1 | 3/2011 | Daniels et al. |
| 2011/0077571 | A1 | 3/2011 | Andresen |
| 2011/0092871 | A1 | 4/2011 | Fabo et al. |
| 2011/0262518 | A1* | 10/2011 | Smyth et al. ............ 424/423 |
| 2011/0275028 | A1 | 11/2011 | Dragan et al. |

OTHER PUBLICATIONS

Aluminum sulfate: retrieved from internet: https://en.wikipedia.org/wiki/Aluminium_sulfate. Retrieved on Aug. 10, 2015.*

Mullite: retrieved from internet: https://en.wikipedia.org/wiki/Mullite. Retrieved on Aug. 12, 2015.*

International Search Report and Written Opinion for PCT/US2012/054928 dated Nov. 19, 2012.

Drug Information Online drugs.com, "Kaolin," Web page <http://www.drugs.com/npp/kaolin.html?printable=1>, 9 pages, dated 2009; retrieved on Dec. 7, 2015.

Supplementary European Search Report for European Application EP 12 83 2223 (European regional phase of PCT/US2012/054928); Apr. 28, 2015.

Office Action for Chinese Application No. 201280044207.8 (Chinese national phase of PCT/US2012/054928); Apr. 3, 2015.

"Kaolinite," Web page <https://en.wikipedia.org/wiki/Kaolinite>, 10 pages, last modified Dec. 1, 2015; retrieved on Dec. 7, 2015.

Yu Song, Clinical External Application Drugs in Dermatology, Heilongjiang People's Publishing House, 1975, p. 22, line 7—p. 24.

Office Action for Chinese Application No. 201280044207.8 (Chinese national phase of PCT/US2012/054928); Feb. 23, 2016.

* cited by examiner

COMPOSITION AND DRESSING FOR WOUND TREATMENT

BACKGROUND

Traditional hemostatic materials include tourniquets, bandages and sterilized dressings. Other hemostatic materials include fibrin glues (FG), oxidized celluloses (OC), oxidized regenerated celluloses (ORC) and mineral zeolite-based hemostats. Fibrin glues are hemostatic adhesives that are biocompatible, and which likely mimic the spontaneous coagulation process while being independent of platelets and coagulation factors. Commercially available fibrin-based glue products include Beriplast P, Hemaseel, Biocol, Boheal and Quixil, etc. However, fibrin glues are costly to produce, may be a source of blood-borne diseases and infections, are complicated to apply and are slow in arresting bleeding.

Oxidized celluloses and oxidized regenerated celluloses are degradable, have antibacterial and hemostatic properties, and are especially effective in arresting slow bleeding. The hemostatic mechanism with these materials is proposed to be that the acidic carboxyl group in the molecule binds with the $Fe^{3+}$ ion in the hemoglobin to generate the acidic $Fe^{3+}$-hemin in blood, whereby red-brown gel blocks are formed to close the end of capillaries thereby arresting the bleeding. Nevertheless, the oxidized celluloses and oxidized regenerated celluloses may expand, which in turn may cause neurothlipsis. Examples of commercially available OC and ORC hemostats include the Oxycel series and the Surgical series.

Inert mineral zeolite particles were first found to have a hemostatic effect in the 1980s (see U.S. Pat. No. 4,822,349). In 2002, Z-Medica Corporation produced a type of new hemostatic material under the name of QuikClot™. These zeolite-based materials are apparently superior to other hemostatic materials in hemostatic efficacy. The hemostatic mechanism of mineral zeolites mainly resides in their extraordinary selective adsorption of water relative to erythrocytes, platelets and other coagulation factors, which leads to a quick hemostasis by concentrating the clotting factors at the injury site. However, mineral zeolite hemostats may be recognized as "foreign" and are not biodegradable.

SUMMARY OF THE INVENTION

The invention provides methods and compositions to reduce or arrest the flow of blood from a wound, e.g., by accelerating clotting, and optionally preventing or inhibiting microbial infection in the wound area, and optionally providing for an analgesic effect in the wound area, or any combination thereof. In one embodiment, the invention provides a substrate, e.g., a protective covering for a wound comprising a composition of the invention. The compositions of the invention promote and accelerate healing as a result of the presence of a combination of agents. In one embodiment, the composition includes an absorbent agent, such as mullite or aluminum silicate, and a blood vessel constricting agent, such as aluminum sulfate or caffeine. The composition may also include a blood clotting agent, e.g. fibrin, in an effective amount. In another embodiment, the composition includes a blood vessel constricting agent, e.g., aluminum sulfate or caffeine, and a blood clotting agent in an effective amount. In one embodiment, the invention provides an anhydrous mixture, e.g., in powder form, comprising a combination of agents forming a composition of the invention. Compositions of the invention can be hydrated in the presence of blood, wound exudate, or other selected liquid or aqueous media which promotes clotting of the blood. In one embodiment, the invention provides a gel comprising a composition of the invention. In one embodiment, the invention provides an aerosol comprising a composition of the invention.

In one embodiment, the invention provides a support, e.g., a bandage or other wound dressing, that includes an absorbent agent (e.g. mullite) and a blood vessel constricting agent, and optionally an antiseptic agent such as an antimicrobial agent, optionally a topical analgesic or anesthetic agent, optionally isolated fibrin or components that yield fibrin, e.g., isolated fibrinogen and isolated thrombin, or any combination of optional component(s). In one embodiment, the invention provides a support that includes a blood vessel constricting agent and isolated fibrin or components that yield fibrin, e.g., isolated fibrinogen and isolated thrombin, and optionally an antiseptic agent such as an antimicrobial agent, and optionally a topical analgesic or anesthetic agent.

Thus, in one embodiment the invention provides a composition for wound healing comprising an amount of aluminum sulfate and an amount of mullite. The composition may also include an amount of a blood clotting agent. In one embodiment, the composition is in powder form. In one embodiment, the composition is in aerosol form. In one embodiment, the composition is in gel form. In one embodiment, the composition is applied to a support, e.g., a bandage. The composition may further include a local anesthetic agent and/or an antiseptic such as an antimicrobial agent.

In another embodiment, the invention provides a composition for wound healing comprising an amount of aluminum sulfate and an amount of fibrin or an amount of fibrinogen and thrombin. In one embodiment, the composition is in powder form. In one embodiment, the composition is in aerosol form. In one embodiment, the composition is in gel form. In one embodiment, the composition is applied to a support, e.g., a bandage. The composition may further include a local anesthetic agent and/or an antiseptic such as an antimicrobial agent.

In another embodiment, the invention provides a composition for wound healing comprising an amount of mullite. The composition may be in any form which may effectively deliver mullite to a wound, such as a powder form, an aerosol form, or a gel form. In one embodiment, the composition is applied to a support, e.g., a bandage. The composition may further include a blood vessel constricting agent, such as aluminum sulfate, a blood clotting agent, such as fibrin, a local anesthetic agent, and/or an antiseptic such as an antimicrobial agent.

In one embodiment, a composition of the invention comprises a gel comprising an absorbent agent and a blood vessel constricting agent, and optionally an antiseptic agent such as an antimicrobial agent, optionally a topical analgesic or anesthetic agent, optionally isolated fibrin or components that yield fibrin, e.g., isolated fibrinogen and isolated thrombin, or any combination of optional components. In one embodiment, a composition of the invention comprises a gel comprising a blood constricting agent and isolated fibrin or components that yield fibrin, e.g., isolated fibrinogen and isolated thrombin, and optionally an antiseptic agent such as an antimicrobial agent, and optionally a topical analgesic or anesthetic agent.

In one embodiment, a composition of the invention comprises an aqueous liquid comprising an absorbent agent (e.g. mullite) and a blood vessel constricting agent, and optionally an antiseptic agent such as an antimicrobial agent, optionally a topical analgesic or anesthetic agent, optionally isolated fibrin or components that yield fibrin, e.g., isolated fibrinogen and isolated thrombin, or any combination of optional component(s). In another embodiment, a composition of the invention comprises an aqueous liquid comprising a blood vessel constricting agent and isolated fibrin or components that yield fibrin, e.g., isolated fibrinogen and isolated thrombin, and optionally an antiseptic agent such as an antimicrobial agent, and optionally a topical analgesic or anesthetic agent.

In one embodiment, the composition of the invention is a solid, e.g., a powder form. In another embodiment, the composition of the invention comprises an aerosol or spray having an absorbent agent (e.g. mullite) and a blood vessel constricting agent, and optionally an antiseptic agent such as an antimicrobial agent, optionally a topical analgesic or anesthetic agent, optionally isolated fibrin or components that yield fibrin, e.g., isolated fibrinogen and isolated thrombin, or a blood vessel constricting agent and isolated fibrin or components that yield fibrin, e.g., isolated fibrinogen and isolated thrombin, and optionally an antiseptic agent such as an antimicrobial agent, and optionally a topical analgesic or anesthetic agent. In one embodiment, a substantially anhydrous composition of the invention is provided. A composition of the invention may be applied as a powder, a liquid, an aerosol or spray, or a dry support, e.g., dressing, having a composition of the invention applied thereto and/or embedded therein.

Also provided are methods of making and using the compositions and supports having the compositions of the invention.

DETAILED DESCRIPTION OF THE INVENTION

The invention relates to devices, e.g., supports such as bandages, and compositions, e.g., gels, aqueous liquids, powders and sprays, to facilitate the reduction in bleeding, to initiate and provide for hemostasis and/or methods of making and using the devices and compositions.

In one embodiment, the invention provides a support, e.g., a bandage or other wound dressing comprising an amount of a blood vessel constricting agent and an amount of isolated fibrin or components that yield fibrin, e.g., isolated fibrinogen and isolated thrombin, optionally an adsorbent or absorbent agent, optionally an antiseptic agent such as an antimicrobial agent, optionally a topical analgesic or anesthetic agent, or any combination of optional components. In another embodiment, the invention provides a support comprising an amount of a blood vessel constricting agent and an amount of an absorbent agent, optionally an amount of isolated fibrin or components that yield fibrin, optionally an antiseptic agent, optionally a topical analgesic or anesthetic agent, or any combination of optional components. A "wound dressing" includes any pharmaceutically acceptable wound covering or support matrix such as, for example, a film, including those of a semipermeable or a semi-occlusive nature such as polyurethane copolymers, acrylamides, acrylates, paraffin, polysaccharides, cellophane and lanolin, and hydrocolloids including carboxymethylcellulose, protein constituents of gelatin, pectin, and complex polysaccharides including Acacia gum, guar gum and karaya. These materials may be utilized in the form of a flexible foam or, in the alternative, formulated in polyurethane or, in a further alternative, formulated as an adhesive mass such as polyisobutylene; starch or propylene glycol; which typically contain about 80% to about 90% water and are conventionally formulated as sheets, powders, pastes and gels in conjunction with cross-linked polymers such as polyethylene oxide, polyvinyl pyrrolidone, acrylamide, propylene glycol; a foam such as polysaccharide which consist of hydrophilic open-celled contact surface and hydrophobic closed-cell polyurethane, and other materials including pine mesh gauze, paraffin and lanolin-coated gauze, polyethylene glycol-coated gauze, knitted viscose, rayon, and polyester and cellulose-like polysaccharide such as alginates, including calcium alginate, which may be formulated as non-woven composites of fibers or spun into woven composites.

In one embodiment, the invention provides a device for promoting the clotting of blood, thereby controlling bleeding. The device comprises a gauze substrate, e.g., cotton cellulose formed as woven or non-woven gauze, and a composition of the invention disposed on the gauze substrate. Upon the application of the device to the bleeding wound, at least a portion of the components of the composition comes into contact with the blood to cause the hemostatic effect. In another embodiment, the bandage has a flexible substrate and a gauze substrate mounted thereon.

According to another aspect, the invention provides a wound dressing, such as a bandage that can be applied to a bleeding wound to promote the clotting of blood, thereby controlling bleeding. In one embodiment, the bandage comprises a substrate, a mesh mounted on the substrate, and a composition of the invention retained in the mesh. The mesh has a plurality of members arranged to define openings that allow for the flow of blood into the mesh and into the composition of the invention, thereby producing a clotting effect.

In one embodiment, a patch bandage comprises an absorbent fiber pad which is backed up by and located at the center of a holding strip, the pad having a composition of the invention applied to the surface and/or embedded therein and the strip having an adhesive surface with the pad being affiliated to the surface. The bandage may be placed over a cut or wound to cover the wound with the pad covering the wound to permit the pad to absorb the blood flow therefrom and permit the adhesive surface of the strip to adhere to the skin and hold the bandage in place. The bandage may be provided in a closed sterile receptacle or container or the like.

In one embodiment, the invention provides a hemostatic sponge that can be applied to a bleeding wound to clot blood and control bleeding. Such a sponge comprises a substrate and a hemostatic composition of the invention disposed on a first surface of the substrate or dispersed in the substrate. Another type of sponge has first and second substrates. A hemostatic composition of the invention is applied to the first substrate, and the second substrate is placed on the hemostatic composition. When this sponge is used to treat a bleeding wound, applying the sponge causes at least a portion of the hemostatic material to come into contact with blood through at least one of the substrates. The hemostatic sponge may comprise a film and a hemostatic composition of the invention incorporated into the film; a substrate, a hemostatic composition of the invention disposed on the substrate, and a film disposed over the hemostatic composition of the invention; or a hemostatic composition of the invention sandwiched between two substrates.

Thus, the composition can be used in solid form (e.g., retained in a mesh or in a film), or it can be used in powder form (e.g., deposited on a fibrous substrate to form a gauze or a sponge).

In one embodiment, the combination of agents disclosed herein greatly enhances blood clotting, inhibits microbial infection, and/or accelerates wound healing, and may be combined with a covering or carrier (support) such as a bandage, cotton gauze and the like. In one embodiment, a wound treated with a composition of the invention is subsequently covered with a suitable wound covering or dressing. In another embodiment, a wound covering or dressing is impregnated or coated with a dry powder form of a composition of the invention and applied to the wound. Thus, the present invention can also be practiced in conjunction with wound coverings, dressings, and protective materials, such as bandages, cotton gauze, and the like.

The invention also concerns kits comprising in one or more containers or packages having a plurality of components for a composition of the invention. In one embodiment, a composition of the invention is packaged in a container that is designed in a manner so as to preserve the anhydrous nature of the composition until the container is opened. A kit of the invention can also comprise a container having a quantity of suitable powder or spray liquid or aqueous media, for application to a wound. In one embodiment, the powder spray or liquid or aqueous media is provided in sterile form. A kit of the present invention can also comprise a wound covering, dressing, or other wound or surgical site protective material, e.g., one maintained in sterile form until the package or container is opened for use.

In one embodiment, a kit comprises a dressing that includes a pad that contains a composition of the invention within and/or on the surface of the pad. In one embodiment, the pad is composed of porous foam that is sufficiently open to allow a free flow of powder to fill the voids in the porous foam. The open voids can either be random (like a foam air conditioning filter) or organized into tunnels. The tunnels can keep compositions from mixing until needed. The tunnels can be round holes or geometric shapes. Around the perimeter of the randomly open foam a less porous border may be used to contain the composition. The pad can be designed so that lateral pressure can compress the foam or tunnels and hold the composition in place for inverted application.

In another embodiment, a kit comprises a dressing having a pad with fibers perpendicularly oriented to the plane of the pad, wherein the fibers can hold and release a composition of the present invention. The dressing can be provided with or without an integrated foam or fabric or substrate backing. The dressing can be pre-loaded with a composition of the present invention. The dressing can be of a design wherein the fibers remain attached to the dressing during and/or after application to a wound or surgical site.

In one embodiment, a kit comprises a wound dressing with a flocked pad wherein the pad has a foam (e.g., polyurethane) portion and a flocked fibers portion. In one embodiment, the foam portion is a porous foam as described above. In this embodiment, a composition of the invention can be loaded onto the side of the foam opposite that of the fibers and the composition could then travel or flow through the foam and onto the fibers. The fibers can be attached to the foam portion and can be made, for example, out of calcium alginate. The fibers can be a woven or non-woven material. The fibers can be composed of any suitable material such as cotton, wool, etc. In one embodiment, the fibers are composed of a velvet fabric. The fibers can be coated or flocked with a composition of the present invention. Optionally, the fibers can be composed of dissolvable material (e.g., polyvinyl alcohol) or a biodegradable material (e.g., starch, calcium alginate, polysaccharides, etc.). In one embodiment, the fibers can be composed of a material that can dissolve in a solution, such as a saline solution. In another embodiment, the fibers themselves do not dissolve in solution but are attached to the pad portion via a substance or material that itself can dissolve in solution. This permits a solution to be contacted with a dressing that has been applied to a site where blood has coagulated and formed a scab, wherein the fibers dissolve or the attachment dissolves and the pad portion of the dressing can then be easily removed without ripping the scab off the wound.

Compositions of the invention may be stored under substantially anhydrous conditions. Compositions of the invention can be provided in a sterile form.

Compositions of the subject invention can also comprise additional optional compounds or agents that provide for anti-microbial, analgesic or anesthetic, increased absorptive, and/or increased wound healing properties.

The dosage or amount of the components of a composition of the invention to be typically administered can be readily determined and will be dependent on various factors, such as the size and type of wound, the amount of blood or fluid present in the wound, and physical characteristics of the patient, as well as other drugs or treatments the patient is receiving.

The compositions of the invention are easy to use and to apply to a wound, likely cause no irritation or allergic responses, and absorb wound exudates (which reduces odors and microbial action at the wound site) and so may also be used to treat lesions, trauma, injuries, incisions, and/or burns wherein stopping or slowing the flow of blood from a wound, incision, or medical treatment site is indicated.

Following application of a composition of the invention, e.g., a spray or gel, the wound may be left exposed to the air, or the wound may optionally be covered with a bandage or other suitable wound covering, e.g., one that includes a composition of the invention.

Exemplary Compositions

Disclosed herein are hemostatic devices and hemostatic agents that are applicable to bleeding wounds to promote hemostasis. In one embodiment, the hemostatic agents generally include absorbent agents such as silica-based materials that, when brought into contact with a bleeding wound, can minimize or stop blood flow by absorbing at least portions of the liquid phases of the blood, thereby facilitating clotting. In one embodiment, the absorbent agent of the invention is mixed with or otherwise used in conjunction with other materials to provide additional clotting functions and/or improved efficacy, including a blood vessel constricting agent, and optionally agents that provide an antiseptic environment at the wound site or to provide functions that are supplemental to the clotting functions, including, but are not limited to, pharmaceutically-active compositions such as antibiotics, antifungal agents, antimicrobial agents, anti-inflammatory agents, analgesics, antihistamines (e.g., cimetidine, chlorpheniramine maleate, diphenhydramine hydrochloride, and promethazine hydrochloride), compounds containing silver or copper ions, combinations of the foregoing, and the like. Other materials that can be incorporated to provide additional hemostatic functions include ascorbic acid, tranexamic acid, rutin, and thrombin. Botanical agents having desirable effects on the wound site may also be added.

In one embodiment, the substrate is an absorbent gauze material that defines a matrix. Other materials from which the substrate may be fabricated include woven fabric, non-woven fabric, paper (e.g., kraft paper and the like), and cellulose material (e.g., cotton in the forms of balls, swabs, and the like), as well as other materials such as rayon/polyester cellulose blends and the like are also within the scope of the present invention.

In one embodiment, a composition of the present invention is woven into the fibers of the substrate. For example, a composition which includes an effective amount of aluminum sulfate and mullite, and which optionally includes other ingredients such as fibrin, a local anesthetic agent, and/or an antiseptic agent, may be woven into the fibers of an absorbent tissue/paper product. The product may then be used in wound cleaning and to blot up blood resulting from minor cuts or scrapes. It may also be used in a bandage or other wound dressing to facilitate blood clotting, to provide an anesthetic effect, and/or to provide an antiseptic effect.

In one embodiment, the invention provides a composition which includes an effective amount of aluminum sulfate and mullite, optionally having isolated fibrin, or isolated fibrinogen and isolated thrombin, and also optionally a local anesthetic agent and/or an antiseptic agent. In one embodiment, a composition of the invention includes an absorbent agent (e.g. mullite) and a blood vessel constricting agent (e.g., aluminum sulfate or caffeine). In one embodiment, a composition of the invention includes an absorbent agent (e.g. mullite), a blood vessel constricting agent (e.g., aluminum sulfate or caffeine), and a local (e.g., topical) anesthetic agent. In one embodiment, a composition of the invention includes an absorbent agent (e.g. mullite), a blood vessel constricting agent (e.g., aluminum sulfate or caffeine), a local anesthetic agent and an antiseptic agent. In one embodiment, a composition of the invention includes an absorbent agent (e.g. mullite), a blood vessel constricting agent (e.g., aluminum sulfate or caffeine), isolated fibrinogen and isolated thrombin (or isolated fibrin). In one embodiment, a composition of the invention includes an absorbent agent (e.g. mullite), a blood vessel constricting agent (e.g., aluminum sulfate or caffeine), isolated fibrinogen and isolated thrombin (or isolated fibrin), and a local anesthetic agent. In one embodiment, a composition of the invention includes an absorbent agent (e.g. mullite) a blood vessel constricting agent (e.g., aluminum sulfate or caffeine), isolated fibrinogen and isolated thrombin (or isolated fibrin), a local anesthetic agent and an antiseptic agent. In one embodiment, the invention provides a bandage, gel or spray having a composition of the invention.

In one embodiment, a composition of the invention has a blood vessel constricting agent (e.g., aluminum sulfate or caffeine) and a local (e.g., topical) anesthetic agent. In one embodiment, a composition of the invention has a blood vessel constricting agent (e.g., aluminum sulfate or caffeine), a local anesthetic agent and an antiseptic agent. In one embodiment, a composition of the invention has a blood vessel constricting agent (e.g., aluminum sulfate or caffeine), isolated fibrinogen and isolated thrombin (or isolated fibrin). In one embodiment, a composition of the invention has a blood vessel constricting agent (e.g., aluminum sulfate or caffeine), isolated fibrinogen and isolated thrombin (or isolated fibrin), and a local anesthetic agent. In one embodiment, a composition of the invention has a blood vessel constricting agent (e.g., aluminum sulfate or caffeine), isolated fibrinogen and isolated thrombin (or isolated fibrin), a local anesthetic agent and an antiseptic. In one embodiment, the invention provides a bandage, gel or spray having a composition of the invention.

In one embodiment, an absorbent agent (e.g. mullite) and a blood vessel constricting agent (e.g., aluminum sulfate and/or caffeine) are in a ratio of 1:1 or 2:1 by volume. In one embodiment, an absorbent agent (e.g. mullite), a blood vessel constricting agent (e.g., aluminum sulfate and/or caffeine), plus a local anesthetic agent such as lidocaine, tetracaine, or benzocaine or prilocaine, are employed in a composition, e.g., one in which the formulation ranges from 1:1 to 2:1 absorbent agent to blood vessel constricting agent, with an effective amount of a local anesthetic agent. In one embodiment, an absorbent agent (e.g. mullite), a blood vessel constricting agent (e.g., aluminum sulfate and/or caffeine), a local anesthetic agent such as lidocaine, tetracaine, or benzocaine, and an antimicrobial, such as neomycin sulfate, polymyxin B, bacitracin zinc, pramoxine or prilocaine, are employed in a composition of the invention. In one embodiment, an absorbent agent (e.g. mullite) a blood vessel constricting agent (e.g., aluminum sulfate and/or caffeine), and isolated fibrinogin and isolated thrombin (or isolated fibrin) are employed in a composition, e.g., one in which the formulation ranges from 1:1 to 2:1 absorbent agent to blood vessel constricting agent, with an effective amount of fibrin. In one embodiment, an absorbent agent, a blood vessel constricting agent, isolated fibrinogin and thrombin (or isolated fibrin), and a local anesthetic agent such as lidocaine, tetracaine, or benzocaine or prilocaine, are employed, in which the formulation ranges from 1:1 to 2:1 absorbent agent to blood vessel constricting agent, with effective amounts of fibrin and a local anesthetic agent. In one embodiment, the composition comprises an absorbent agent (e.g. mullite), a blood vessel constricting agent (e.g., aluminum sulfate and/or caffeine), isolated fibrinogin and isolated thrombin (or isolated fibrin), a local anesthetic agent such as lidocaine, tetracaine, or benzocaine or prilocaine, and an antimicrobial antiseptic such as neomycin sulfate, polymyxin B, bacitracin zinc, or pramoxine, are employed. An exemplary formulation range is from 1:1 to 2:1 absorbent agent to blood vessel constricting agent, with effective amounts of fibrin, a local anesthetic agent, and an antiseptic agent.

In one embodiment, to deliver the therapeutic agents, a powder may be used to quickly clot blood when applied directly to minor cut or scrapes. In one embodiment, a powder is available in spray form. In one embodiment, the powder is woven in fibers of pad in adhesive bandage or gauze. Other substances may also be woven into fibers of pad in adhesive bandages or gauze or fibers of paper like tissue to be used for blotting (added to facial tissue or smaller tissues similar to those used for facial oil absorbing). In one embodiment, a component may be adhered to a pad in adhesive bandage using bonding agent (e.g., glycerin). In one embodiment, the substance added to an antiseptic dispensing device or composition (gel, liquid, or spray). In one embodiment, a powder is compressed into stick form or into a mold that is packaged along with a disposable applicator. In one embodiment, the composition is available in a snap q-tip form (plastic tube in the middle, snapped releases substance to cotton tip for application).

To prepare compositions in accordance with the present invention, the individual components were combined to result in the composition. The components may be combined using any method that does not negatively affect the functionality of each component and provides uniform or nearly uniform distribution of the components in the composition, such as but not limited to mixing under shear forces or under agitation. The components used in the composition are of pharmaceutically or medically acceptable purity.

EXAMPLES

Compositions Including Kaolin

Example 1

Kaolin and Aluminum Sulfate

Testing was conducted using a powder composition including a mixture of kaolin (i.e. aluminum silicate hydroxide) and aluminum sulfate, wherein the kaolin and aluminum sulfate were present at a 1:1 ratio by volume. Cuts similar in size and depth were made to the right and left index fingers of a human subject using a razor blade. The powder composition was applied to a bandage, which was then placed over the cut on the left index finger. A plain bandage, which did not include the powder composition, was placed over the cut on the right index finger. Both of the bandages were removed after 1 minute and the cuts were visually inspected. After 1 minute, the cut on the left index finger, to which a bandage including the powder composition had been applied, had stopped bleeding entirely. However, after the same amount of time, the cut on the right index finger, to which a bandage without the powder composition had been applied, continued to bleed. Similar results were also obtained by applying the powder composition to cuts on the ankle and leg of a human subject.

Further testing was conducted by applying the powder composition, which included a mixture of kaolin and aluminum sulfate at a 1:1 ratio by volume, directly to cuts on a human subject without using a bandage. This further testing showed that the application of the powder composition without a bandage was also effective in stopping the bleeding from cuts, and in facilitating the healing of wounds.

To determine whether another powder composition that could absorb moisture would be effective in stopping the bleeding from cuts, a sample of flour was applied to a cut on a human subject. The testing showed that the application of flour was not effective in stopping the bleeding from cuts.

Testing was also conducted using kaolin and aluminum sulfate individually to treat cuts on a human subject. It was unexpectedly found that the combination of kaolin and aluminum sulfate was significantly more effective in healing wounds than either of these components alone. While not intending to be bound by theory, it is believed that the combination of kaolin and aluminum sulfate works synergistically to stop blood flow by removing blood from the wound, constricting blood vessels, and stimulating the coagulation cascade to produce blood clotting.

Examples

Compositions Including Mullite

The following examples involve compositions including mullite and aluminum sulfate. The mullite used in these examples had the formula $Al_6O_{13}Si_2$, and was obtained from Sigma-Aldrich Corp., St. Louis, Mo., United States. The aluminum sulfate was obtained from Chemistrystore.com Inc., Cayce, S.C., United States. The percentages of mullite and aluminum sulfate reported in the following examples, such as 50% mullite and 50% aluminum sulfate, are percentages reported by volume. Specifically, to prepare a 50% mullite and 50% aluminum sulfate mixture, equal volumes of each component were used. A volume of approximately 3 tablespoons, or about 44.4 mL, of each component was used to prepare a small batch of a 50% mullite and 50% aluminum sulfate mixture. Three small batches were combined to prepare a large batch of approximately 18 tablespoons, or about 266.4 mL.

To prepare each mixture, the mullite and aluminum sulfate were initially mixed together by hand using a spoon, and then placed in a closed container and agitated for approximately one minute. Each mixture was visually inspected to confirm that it was substantially homogeneous.

Example 2

Mullite and Aluminum Sulfate

Testing was conducted using powder compositions including mullite and aluminum sulfate. Three different compositions were tested: composition 1, which was comprised of 25% mullite and 75% aluminum sulfate; composition 2, which was comprised of 50% mullite and 50% aluminum sulfate; and composition 3, which was comprised of 75% mullite and 25% aluminum sulfate. Tests were conducted by applying the powder compositions to cuts on animal subjects (rabbits and rats). The incisions were each 1 cm in length, and were made using a surgical knife. Each incision was made to a depth at which consistent bleeding occurred along the length of the incision. After each incision was made, the incision was blotted once, and then a timer clock was started. A powder composition was then applied to the incision. A sufficient amount of powder composition was used to cover the entire incision. It was found that 1/16 (0.0625) of a teaspoon of the powder composition, or about 0.308 mL, was sufficient, although it is contemplated that more or less may be used depending on the size and depth of the incision. The amount of time from the starting of the timer clock to the cessation of bleeding was measured. The cessation of bleeding was determined by visual inspection.

Control tests were also conducted on animal subjects (rabbits and rats). In the control tests, after each incision was made, the incision was blotted once and then a timer clock was started. The amount of time from the starting of the timer clock to the cessation of bleeding was measured. The cessation of bleeding was determined by visual inspection. In the control tests, no composition was applied to the incisions.

Each of the three compositions were effective in quickly stopping the bleeding from minor cuts. The composition which caused a cessation in bleeding in the shortest amount of time was composition 2, comprised of 50% mullite and 50% aluminum sulfate. When composition 2 was applied to minor cuts, bleeding stopped in an average amount of time of 17 seconds. Generally, the bleeding stopped almost immediately when composition 2 was applied, but because the timer clock was started just prior to the application of the composition, the measured amount of time included the time required to apply the composition. In contrast, when the control tests were conducted, bleeding stopped in an average of 1 minute and 34 seconds. Therefore, the test results showed that there was an 82% improvement in healing rate when composition 2 was used, in comparison to the control tests.

Accordingly, the testing showed that a composition comprising mullite and aluminum sulfate significantly shortened the amount of time required to stop the bleeding from minor cuts. Of the compositions tested, the composition which stopped the bleeding from cuts most quickly was a composition including mullite and aluminum sulfate in a 1:1 ratio by volume. While not intending to be bound by theory, it is believed that the combination of mullite and aluminum sulfate works synergistically to stop blood flow by removing moisture from the wound, constricting blood vessels, and stimulating the coagulation cascade to produce blood clotting.

Example 3

Mullite/Aluminum Sulfate Composition Compared to Commercially Available Styptic Powder Testing was conducted to compare a mullite/aluminum sulfate composition made in accordance with the present invention to a commercially available styptic powder. The mullite/aluminum sulfate composition was a powder composition comprising 50% mullite and 50% aluminum sulfate. The commercially available styptic powder was Kwik Stop® styptic powder, which is indicated for use on animals, and is available from Gimborn Pet Specialties, Atlanta, Ga., United States. Tests were conducted by applying the powder compositions to cuts on animal subjects (rabbits and rats). The incisions were each 1 cm in length, and were made using a surgical knife. Each incision was made to a depth at which consistent bleeding occurred along the length of the incision. After each incision was made, the incision was blotted once, and then a timer clock was started. A powder composition was then applied to the incision. A sufficient amount of powder composition was used to cover the entire incision. It was found that 1/16 (0.0625) of a teaspoon, or about 0.308 mL, was sufficient, although it is contemplated that more or less may be used depending on the size and depth of the incision. The amount of time from the starting of the timer clock to the cessation of bleeding was measured. The cessation of bleeding was determined by visual inspection.

Control tests were conducted on the same animal that was treated with the Kwik Stop® styptic powder. In the control tests, after each incision was made, the incision was blotted once and then a timer clock was started. The amount of time from the starting of the timer clock to the cessation of bleeding was measured. The cessation of bleeding was determined by visual inspection. In the control tests, no composition was applied to the incisions.

The composition which caused a cessation in bleeding in the shortest amount of time was the mullite/aluminum sulfate composition. When this composition was applied to minor cuts, bleeding stopped in an average amount of time of 17 seconds. In contrast, when the Kwik Stop® styptic powder was applied to a minor cut, bleeding stopped in an average amount of time of 35 seconds. When the control test was conducted, bleeding stopped in an average amount of time of 48 seconds. Therefore, the test results showed that there was a 51% improvement in healing rate when composition 2 was used, in comparison to Kwik Stop® styptic powder. The test results also showed that, in comparison to the control tests, there was a 27% improvement in healing rate when Kwik Stop® styptic powder was used, and a 65% improvement in healing rate when composition 2 was used.

Example 4

Use of Mullite/Aluminum Sulfate Composition to Improve Healing Over Time

Testing was conducted to determine whether a mullite/aluminum sulfate composition made in accordance with the present invention would improve healing over time, in comparison to a commercially available styptic powder. The mullite/aluminum sulfate composition was a powder composition comprising 50% mullite and 50% aluminum sulfate. The commercially available styptic powder was Kwik Stop® styptic powder, which is indicated for use on animals, and is available from Gimborn Pet Specialties, Atlanta, Ga., United States. Tests were conducted by applying the powder compositions to incisions on the backs of animal subjects (rabbits). The incisions were each 1 cm in length, and were made using a surgical knife. Each incision was made to a depth at which consistent bleeding occurred along the length of the incision. A sufficient amount of powder composition was applied to the incision to cover the entire wound. It was found that 1/16 (0.0625) of a teaspoon, or about 0.308 mL, was sufficient, although it is contemplated that more or less may be used depending on the size and depth of the incision. A control test was also conducted, in which no composition was applied to an incision on the back of an animal (rabbit) subject. The animal subjects were then observed for a 14 day period and monitored for healing side effects, including discharge, bruising, swelling, increased temperature at the wound site, and erythema.

The healing side effects observed were as follows. In the control test, very mild swelling was present on day one, and mild erythema was present on days one through ten. In the test in which Kwik Stop® styptic powder was applied, mild swelling was present on days two through seven, and mild erythema was present on days one through eight. In the test in which the mullite/aluminum sulfate composition was applied, very mild swelling and mild erythema were present on day one. Therefore, the mullite/aluminum sulfate composition reduced the duration of healing side effects, in comparison to the Kwik Stop® styptic powder and in comparison to the results of a control test.

Example 5

Use of Mullite/Aluminum Sulfate Composition to Stop Bleeding from a Major Artery Testing was conducted to determine whether a mullite/aluminum sulfate composition made in accordance with the present invention would be effective in stopping the bleeding from an incision of a major artery. The mullite/aluminum sulfate composition was a powder composition comprising 50% mullite and 50% aluminum sulfate. The test of the mullite/aluminum sulfate composition was conducted by applying the powder composition to an incision of the auricular artery of a rabbit and measuring the amount of time required for the cessation of active bleeding. The auricular artery was cut through a cross section to create the incision. No pressure was added to the wound. A sufficient amount of powder composition was used to cover the entire incision. It was found that 1/16 (0.0625) of a teaspoon, or about 0.308 mL, was sufficient, although it is contemplated that more or less may be used depending on the size and depth of the incision. The amount of time was measured by starting a timer clock, applying the powder composition to the wound, blotting the wound after 20 seconds had elapsed, reapplying the powder composition, and stopping the clock when active bleeding from the artery ceased. The total amount of time measured, from the time the clock was started to the time active bleeding ceased, as determined by visual inspection, was 2 minutes and 15 seconds. Accordingly, the testing found that the mullite/aluminum sulfate composition of the present invention was able to effect the clotting of blood from serious wounds.

For comparison, a test using fibrin was also conducted. The fibrin was a commercially available lyophilized fibrin in powder form. The fibrin test was conducted by applying the lyophilized fibrin to an incision of the auricular artery of a rabbit and measuring the amount of time required for the cessation of active bleeding. The auricular artery was cut through a cross section to create the incision. No pressure was added to the wound. A sufficient amount of powder composition was used to cover the entire incision. It was found that 1/16 (0.0625) of a teaspoon, or about 0.308 mL, was sufficient, although it is contemplated that more or less may be used depending on the size and depth of the incision. The amount of time was measured by blotting the wound, starting the timer clock, applying the fibrin to the wound, and stopping the clock when active bleeding from the artery ceased. The total amount of time measured, from the time the clock was started to the time active bleeding ceased, as determined by visual inspection, was 1 minute and 24 seconds.

In the fibrin test, as discussed above, the fibrin remained on the wound for the duration of the test, while in the mullite/aluminum sulfate test, the composition was not on the wound for the duration of the test because the composition was removed and reapplied. Therefore, even though a greater amount of time was measured in the mullite/aluminum sulfate test, the testing showed that the effectiveness of the mullite/aluminum sulfate composition was similar to that of fibrin, in clotting the blood from a major artery. These results are significant because the fibrin used in the testing cost more than 1,000 times as much as the mullite/aluminum sulfate composition used in the testing.

Example 6

Use of Mullite/Aluminum Sulfate/Fibrin Composition

Testing was conducted to determine whether adding fibrin to a mullite/aluminum sulfate composition of the present invention would improve the effectiveness of the composition. The mullite/aluminum sulfate composition was a powder composition comprising 50% mullite and 50% aluminum sulfate. Fibrin in freeze dried form was added to this composition at a 1:1 ratio by volume, resulting in a composition comprising 25% mullite, 25% aluminum sulfate, and 50% fibrin. Both the mullite/aluminum sulfate composition without added fibrin and the mullite/aluminum sulfate composition with added fibrin were tested. Tests were conducted by applying the powder compositions to minor cuts on animal subjects (rabbits and rats). The incisions were each 1 cm in length, and were made using a surgical knife. Each incision was made to a depth at which consistent bleeding occurred along the length of the incision. After each incision was made, the incision was blotted once, and then a timer clock was started. A powder composition was then applied to the incision. A sufficient amount of powder composition was used to cover the entire incision. It was found that ¹⁄₁₆ (0.0625) of a teaspoon, or about 0.308 mL, was sufficient, although it is contemplated that more or less may be used depending on the size and depth of the incision. The amount of time from the starting of the timer clock to the cessation of active bleeding was measured. The cessation of bleeding was determined by visual inspection.

Both of the compositions were effective in quickly stopping the bleeding from minor cuts. When the mullite/aluminum sulfate composition without added fibrin was applied to minor cuts, bleeding stopped in an average amount of time of 17 seconds. When the mullite/aluminum sulfate composition with added fibrin was applied to minor cuts, bleeding stopped in an average amount of time of 13 seconds. Therefore, the addition of fibrin to the mullite/aluminum composition did not significantly improve effectiveness in stopping the bleeding from minor cuts.

Testing was also conducted to determine whether adding fibrin to a mullite/aluminum sulfate composition would improve healing over time. The mullite/aluminum sulfate composition was a powder composition comprising 50% mullite and 50% aluminum sulfate. Fibrin in freeze dried form was added to this composition at a 1:1 ratio by volume, resulting in a composition comprising 25% mullite, 25% aluminum sulfate, and 50% fibrin. Both the mullite/aluminum sulfate composition without added fibrin and the mullite/aluminum sulfate composition with added fibrin were tested. Tests were conducted by applying the powder compositions to incisions on the backs of animal subjects (rabbits). The animal subjects were then monitored for healing side effects, including discharge, bruising, swelling, increased temperature at the wound site, and erythema.

In the test of the mullite/aluminum sulfate composition without added fibrin, very mild swelling an mild erythema were present on day one. No healing side effects were observed after day one. In the test of the mullite/aluminum sulfate composition with added fibrin, discharge and swelling were observed on days one and two, and erythema was observed on days one through three. Therefore, fewer healing side effects were observed when the mullite/aluminum sulfate composition without added fibrin was used, in comparison to the composition with added fibrin.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A composition for wound healing, comprising:
   a substantially homogeneous mixture comprising an amount of mullite, wherein the amount of mullite is effective to promote blood clot formation, an amount of aluminum sulfate, and a blood clotting agent;
   wherein the composition is in powder form.

2. A hemostatic device comprising a support and the composition of claim 1.

3. The composition of claim 1, wherein the blood clotting agent is fibrin.

4. The composition of claim 1, wherein the amount of aluminum sulfate by volume is at least approximately 50% of a total volume of the composition.

5. The composition of claim 4, wherein the blood clotting agent is fibrin.

6. The composition of claim 1, further comprising a local anesthetic agent.

7. The composition of claim 1, further comprising an antimicrobial agent.

8. A composition for wound healing, consisting essentially of:
   an amount of mullite, wherein the amount of mullite is effective to promote blood clot formation,
   an amount of aluminum sulfate, and a blood clotting agent;
   wherein the composition is a substantially homogeneous mixture in powder form.

9. The composition of claim 1, wherein the amount of aluminum sulfate by volume is at least approximately 25% of a total volume of the composition.

10. A hemostatic device comprising a support and the composition of claim 8.

11. The composition of claim 8, wherein the amount of aluminum sulfate by volume is at least approximately 25% of a total volume of the composition.

12. The composition of claim 8, wherein the amount of aluminum sulfate by volume is at least approximately 50% of a total volume of the composition.

13. The composition of claim 8, wherein the blood clotting agent is fibrin.

14. The composition of claim 8, further comprising a local anesthetic agent.

15. The composition of claim 8, further comprising an antimicrobial agent.

* * * * *